US012226509B2

(12) United States Patent
Lorant et al.

(10) Patent No.: US 12,226,509 B2
(45) Date of Patent: Feb. 18, 2025

(54) COSMETIC COMPOSITION COMPRISING A PASTY FATTY SUBSTANCE AND A NON-IONIC DERIVATIVE OF HYDROPHOBIC-MODIFIED CELLULOSE

(71) Applicant: L'OREAL, Paris (FR)

(72) Inventors: Raluca Lorant, Thiais (FR); Mathieu Chabrillangeas, Paris (FR); Nathalie Boileau-Lété, Bondoufle (FR); Sonia Eyraud, Maison-Alfort (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/900,833

(22) PCT Filed: Jul. 4, 2014

(86) PCT No.: PCT/FR2014/051721
§ 371 (c)(1),
(2) Date: Dec. 22, 2015

(87) PCT Pub. No.: WO2015/001270
PCT Pub. Date: Jan. 8, 2015

(65) Prior Publication Data
US 2017/0035673 A1 Feb. 9, 2017

(30) Foreign Application Priority Data

Jul. 4, 2013 (FR) .................................. 1356541
Jul. 4, 2013 (FR) .................................. 1356543

(51) Int. Cl.
| | | |
|---|---|---|
| A61K 8/60 | (2006.01) | |
| A61K 8/06 | (2006.01) | |
| A61K 8/31 | (2006.01) | |
| A61K 8/34 | (2006.01) | |
| A61K 8/36 | (2006.01) | |
| A61K 8/73 | (2006.01) | |
| A61K 8/81 | (2006.01) | |
| A61K 8/86 | (2006.01) | |
| A61K 8/92 | (2006.01) | |
| A61Q 19/00 | (2006.01) | |
| A61Q 19/08 | (2006.01) | |

(52) U.S. Cl.
CPC .............. *A61K 8/602* (2013.01); *A61K 8/062* (2013.01); *A61K 8/31* (2013.01); *A61K 8/345* (2013.01); *A61K 8/36* (2013.01); *A61K 8/731* (2013.01); *A61K 8/8111* (2013.01); *A61K 8/86* (2013.01); *A61K 8/922* (2013.01); *A61Q 19/00* (2013.01); *A61Q 19/007* (2013.01); *A61Q 19/08* (2013.01); *A61K 2800/594* (2013.01); *A61K 2800/596* (2013.01); *A61K 2800/74* (2013.01)

(58) Field of Classification Search
None
See application file for complete search history.

(56) References Cited

U.S. PATENT DOCUMENTS

| | | | | |
|---|---|---|---|---|
| 5,788,954 | A * | 8/1998 | Bonda ...................... | A61K 8/35 424/400 |
| 2005/0026795 | A1 | 2/2005 | Filippi | |
| 2008/0003191 | A1 | 1/2008 | Simonnet et al. | |
| 2010/0086502 | A1* | 4/2010 | Lucet-Levannier ..... | A61K 8/35 424/60 |

FOREIGN PATENT DOCUMENTS

| | | | |
|---|---|---|---|
| EP | 1752135 | * | 8/2006 |
| JP | 2003-238332 A | | 8/2003 |
| JP | 2005-036005 A | | 2/2005 |
| JP | 2005-526118 A | | 9/2005 |
| JP | 2006-028153 A | | 2/2006 |
| JP | 2008-013559 A | | 1/2008 |
| JP | 2008-056619 A | | 3/2008 |
| JP | 2011-511824 A | | 4/2011 |
| JP | 2012-516866 A | | 7/2012 |
| JP | 2013-544830 A | | 12/2013 |
| WO | WO 03/094867 A1 | | 11/2003 |
| WO | WO 2009/101113 A2 | | 8/2009 |
| WO | WO 2010/089199 A1 | | 8/2010 |
| WO | WO 2012/084701 A2 | | 6/2012 |

OTHER PUBLICATIONS

Vippagunta et al. "Crystalline Solids," Advanced Drug Delivery Reviews, 2001, 48, pp. 18.*
English translation of EP1752135.*
SAAPedia, "Hydrogenated Castor Oil Dimer Dilinoleate", 2012, retrieved from http://www.saapedia.org/en/saa/?type=detail&id=2830.*

\* cited by examiner

*Primary Examiner* — Jianfeng Song
(74) *Attorney, Agent, or Firm* — POLSINELLI PC

(57) ABSTRACT

Provided is a composition, in the form of an emulsion comprising a polyester from the esterification, with a polycarboxylic acid, of an aliphatic hydroxycarboxylic acid ester comprising at least two hydroxyl groups and at least one nonionic cellulose derivative comprising one or more hydrophobic substituents containing from 8 to 30 carbon atoms. Also provided is a composition comprising an active agent chosen from C-glucoside derivatives, a pasty fatty substance and a nonionic cellulose derivative comprising one or more hydrophobic substituents containing from 8 to 30 carbon atoms. Emulsions are made possible containing pasty fatty substances that are stable, even without an emulsifying surfactant or with a low content thereof (for example less than 3%), and which afford good sensory pleasure, even when the composition comprises a high content of pasty fatty substances. The emulsions can also contain active agents chosen from C-glucoside derivatives and cucurbic acid derivatives that are stable.

10 Claims, No Drawings

12,226,509 B2

COSMETIC COMPOSITION COMPRISING A PASTY FATTY SUBSTANCE AND A NON-IONIC DERIVATIVE OF HYDROPHOBIC-MODIFIED CELLULOSE

CROSS REFERENCE TO RELATED APPLICATIONS

This application is a National Phase filing under 35 U.S.C. § 371 of PCT/FR2014/051721 filed on Jul. 4, 2014; and this application claims priority to Application No. 1356543 filed in France on Jul. 4, 2013; and this application claims priority to Application No. 1356541 filed in France on Jul. 4, 2013. The entire contents of each application are hereby incorporated by reference.

The invention relates to a composition of emulsion type, in particular a cosmetic composition intended for keratin materials, especially for the skin and the lips, the hair and the nails. The invention also relates to the use of said composition in cosmetics or dermatology, and in particular for the care, hygiene, protection and/or making-up of body or facial skin, or for haircare.

In the cosmetic field, and more particularly in the field of skincare, makeup and photoprotection, it is common practice to use galenical architectures comprising a fatty phase containing solid fatty substances. These galenical forms are usually anhydrous (for example lipsticks) and, on rarer occasions, emulsified. In the latter case, the content of solid fatty substances is quite low (<3%), mainly for reasons of stability of the emulsions and for sensory qualities (provision of a sticky, tacky and greasy effect).

The use of pasty fatty substances in emulsions is, however, particularly advantageous. Specifically, they make it possible to provide nutrition, comfort and persistence effects that are advantageous for treating the skin (in particular dry skin) while at the same time affording better sensory pleasure than anhydrous compositions. Specifically, unlike anhydrous products that are greasy, tacky and lack freshness, emulsions containing pasty fatty substances are nutritive and afford much better sensory pleasure.

Emulsions containing pasty fatty substances are difficult to stabilize. To achieve this, a person skilled in the art often resorts to the use of high contents of emulsifying surfactants. These surfactants are known for their stabilizing efficacy, but often pose problems of discomfort, harmfulness and/or sensory displeasure.

Thus, the introduction of pasty fatty substances into an emulsion, in particular the introduction of high contents of pasty fatty substances, very rapidly brings about an impairment in the stability of the emulsion, particularly of emulsions with no, or with a low content of, emulsifying surfactant.

The need thus remains to prepare compositions simultaneously having:
  pasty fatty substances for their intrinsic benefits;
  good sensory qualities even when the content of pasty fatty substance is high (>3%);
  good stability of the emulsions even when the content of emulsifying surfactant is low or when the emulsion is free of emulsifying surfactant.

Moreover, in the field of formulating antiaging care products, one of the major challenges is to introduce into emulsions efficient biological active agents while at the same time providing (or maintaining) a good level of sensory qualities and of cosmetic pleasantness so as to encourage the use of these products and thus to intensify their effects observed on the skin by virtue of regular and repeated use.

Active agents chosen from C-glucoside derivatives, in particular C-beta-D-xylopyranoside-2-hydroxypropane, and active agents chosen from cucurbic acid derivatives, such as the sodium salt of 3-hydroxy-2-pentylcyclopentaneacetic acid, are active molecules that are particularly effective for treating the problems of aging of the skin.

To obtain high performance levels, these active agents may be used in high contents (for example at contents of 3-10% of C-beta-D-xylopyranoside-2-hydroxpropane active material and 1-5% of 3-hydroxy-2-pentylcyclopentylacetic acid sodium salt active material).

However, these particularly effective active agents may pose sensory quality problems such as the provision of a tacky and/or coarse effect on the skin and the appearance of fluffing during the application phase and/or after penetration of the product into the skin. These drawbacks are without doubt accentuated by the presence of glycols used as "solvent" for the active molecule.

Another challenge for the formulator of antiaging care products is to propose textures that are pleasant and suitable in terms of sensory qualities for the target consumers. Specifically, the consumers who are liable to use antiaging care products have problematics and specific sensory needs regarding their skin, for instance the need for rich, nutritive, soothing and moisturizing textures.

Finally, the introduction of active agents of this type into emulsified galenical forms causes problems of destabilization of the emulsions, this instability possibly going as far as phase separation of the emulsion.

The need thus remains to propose skincare compositions that:
  are enriched in active molecules;
  are stable;
  afford a good level of sensory pleasure.

The Applicant has found, surprisingly, that the combination of a particular pasty fatty substance and of at least one hydrophobic-modified cellulose-based gelling agent makes it possible to obtain stable emulsions even without the use of an emulsifying surfactant or with a low content of emulsifying surfactant (for example less than 3%), and affords good sensory pleasure. In particular, when the content of pasty fatty substance is high, this combination makes it possible to avoid the drawbacks of the known products comprising high contents of pasty fatty substances, for instance a greasy or tacky effect on the skin.

The Applicant has also found, surprisingly, that the formulation of active agents chosen from C-glucoside derivatives and cucurbic acid derivatives in an emulsion comprising a combination of a pasty fatty substance and of at least one hydrophobic-modified cellulose-based gelling agent makes it possible to obtain stable emulsions even without the use of an emulsifying surfactant or with a low content of emulsifying surfactant (for example less than 3%), and affords good sensory pleasure without affecting the antiaging activity of the active agents thus formulated. In particular, even when the content of active agents in the emulsion is high, the composition does not comprise the drawbacks of the known products comprising high contents of active agents, for instance sensory quality problems such as the provision of a tacky and/or coarse effect on the skin and the appearance of fluffing during the application phase and/or after penetration of the product into the skin.

Thus, a first subject of the present invention is a cosmetic composition in the form of an emulsion comprising at least one polyester resulting from the esterification, with a polycarboxylic acid, of an aliphatic hydroxycarboxylic acid ester comprising at least two hydroxyl groups and at least one nonionic cellulose derivative comprising one or more hydrophobic substituents containing from 8 to 30 carbon atoms.

A second subject of the present invention is a cosmetic composition in the form of an emulsion comprising at least one active agent chosen from C-glucoside derivatives, in particular C-beta-D-xylopyranoside-2-hydroxypropane, and cucurbic acid derivatives, such as the sodium salt of 3-hydroxy-2-pentylcyclopentyl)acetic acid, at least one pasty fatty substance and at least one nonionic cellulose derivative comprising one or more hydrophobic substituents containing from 8 to 30 carbon atoms.

As the compositions of the invention are intended for topical application to the skin or the integuments, they comprise a physiologically acceptable medium, i.e. a medium that is compatible with all keratin materials, such as the skin, the nails, mucous membranes and keratin fibers (such as the hair or the eyelashes).

The present invention makes it possible to obtain emulsions containing pasty fatty substances that are stable, even without the use of an emulsifying surfactant or with a low content of emulsifying surfactant (for example less than 3%), and which afford good sensory pleasure, even when the composition comprises a high content of pasty fatty substances.

Thus, it is possible to introduce into the composition in accordance with the invention high contents of pasty fatty substances without impairing its stability, so as to obtain, for example, a composition for caring for dry skin which can make up for the lack of skin lipids of dehydrated skin, provide persistent nutrition and comfort by means of good film-forming properties, while at the same time having good sensory properties, for example a non-greasy and non-tacky effect and a matt appearance of the skin, and also good skin-penetrating properties.

The present invention also makes it possible to obtain emulsions containing active agents chosen from C-glucoside derivatives and cucurbic acid derivatives that are stable, even without the use of an emulsifying surfactant or with a low content of emulsifying surfactant (for example less than 3%), and which afford good sensory pleasure, even when the composition comprises a high content of these active agents. The composition according to the invention affords excellent sensory qualities, without a coarse or greasy or tacky effect and without a fluffing effect.

Furthermore, it can reinforce the perception of efficacy by means of immediate effects felt as soon as the product is applied: nutritive, soothing, moisturizing effects.

Thus, it is possible to introduce into the composition in accordance with the invention high contents of active agents chosen from C-glucoside derivatives and cucurbic acid derivatives without impairing its stability, while at the same time having good sensory properties, for example a non-tacky and non-coarse effect without the appearance of fluffing on application and after penetration of the product into the skin, so as to obtain, for example, an antiaging care composition for keratin materials, and in particular for the skin, which has good performance qualities.

Moreover, when the composition comprises one or more fillers with an optical effect and/or one or more pigments, it affords matt-effect and soft-focus properties on the skin even when the content of pasty fatty substances and/or when the content of active agents in the composition is high. Furthermore, the composition according to the invention has the advantage of not causing fluffing when it is applied to the skin and/or after it has penetrated into the skin. All in all, the working properties are improved.

Another subject of the present invention is a cosmetic process for making up and/or caring for keratin materials, comprising a step of applying a composition as defined above to said keratin materials.

In the text hereinbelow, the expression "at least one" is equivalent to "one or more" and, unless otherwise indicated, the limits of a range of values are included in that range.

Polyesters

According to the first subject of the invention, the composition comprises at least one polyester resulting from the esterification, with a polycarboxylic acid, of an aliphatic hydroxycarboxylic acid ester comprising at least two hydroxyl groups.

The polyester according to the invention is a copolymer which results from the esterification, with a polycarboxylic acid, of an aliphatic hydroxycarboxylic acid ester (which will be referred to hereinbelow as a "hydroxy ester").

The polyester according to the invention preferably has a molecular weight between 3000 and 7000 g/mol. For example, Risocast DA-L has a number-average molecular mass of between 3500 and 4000 g/mol and Risocast DA-H has a number-average molecular mass of between 5000 and 6500 g/mol. These products are sold by the Japanese company Kokyu Alcohol Kogyo.

The mole ratio between the polycarboxylic acid and the hydroxy ester used for preparing the polyester according to the invention is preferably between 0.25 and 1. For example, this ratio is equal to 0.75 for Risocast DA-H, and this ratio is equal to 0.5 for Risocast DA-L.

As polyesters that may be used in the composition according to the invention, mention may be made in particular of:
  the ester resulting from the esterification reaction of hydrogenated castor oil with dilinoleic acid in proportions of 2 to 1,
  the ester resulting from the esterification reaction of hydrogenated castor oil with isostearic acid in proportions of 4 to 3.

The polyester of the present invention is advantageously a pasty or viscous compound at room temperature (25° C.). For the purposes of the present invention, the term "pasty" is intended to denote a lipophilic fatty compound with a reversible solid/liquid change of state, and comprising at a temperature of 23° C. a liquid fraction and a solid fraction.

For the purposes of the invention, the term "pasty compound" means a compound preferably having a hardness at 20° C. ranging from 0.001 to 0.5 MPa and preferably from 0.002 to 0.4 MPa.

By way of example, Risocast DA-L has a hardness at 20° C. of 0.04 MPa, a liquid fraction at 23° C. equal to 82% and a liquid fraction at 32° C. equal to 90%.

The polyester according to the invention results from the esterification:
  of a polycarboxylic acid, and
  of an aliphatic hydroxycarboxylic acid ester (which will be referred to hereinbelow as a "hydroxy ester").

Hydroxy Ester

The aliphatic hydroxycarboxylic acid ester (or hydroxy ester) comprises at least two hydroxyl groups.

The hydroxy ester is advantageously derived from the reaction of at least one aliphatic hydroxycarboxylic acid with a polyol.

Said aliphatic hydroxy acid especially comprises from 2 to 40 carbon atoms, preferably from 10 to 34 carbon atoms and better still from 12 to 28 carbon atoms; it also comprises from 1 to 20 hydroxyl groups, preferably from 1 to 10 hydroxyl groups and better still from 1 to 6 hydroxyl groups, which may be subsequently esterified with the polycarboxylic acid to obtain the polyester of the present invention.

Said polyol may comprise from 2 to 40 carbon atoms and better still from 3 to 30 carbon atoms. The polyol is preferably an aliphatic polyol. Advantageously, the polyol is not a saccharide.

Said polyol which reacts with the hydroxy acid described previously may be partially or totally esterified; advantageously, the polyol is totally esterified.

Preferably, the aliphatic hydroxycarboxylic acid ester is a hydroxy fatty acid ester such that the fatty acid residue comprises at least 12 carbon atoms, for example from 12 to 40 carbon atoms and better still from 12 to 28 carbon atoms.

The aliphatic hydroxycarboxylic acid ester that may be used in the invention may be chosen from:

a) partial or total esters of saturated linear aliphatic monohydroxy monocarboxylic acids;

b) partial or total esters of unsaturated aliphatic monohydroxy monocarboxylic acids such as glyceryl triricinoleate (castor oil);

c) partial or total esters of $C_2$ to $C_{16}$ aliphatic polyol which has reacted with a monohydroxy or polyhydroxy aliphatic monocarboxylic or polycarboxylic acid, especially such as triglycerides, pentaerythrityl, trimethylolpropane, propylene glycol, neopentyl glycol, dipentaerythrityl or polyglyceryl esters, and sorbitol esters;

and mixtures thereof.

Advantageously, when the aliphatic hydroxycarboxylic acid ester results from the esterification of an aliphatic polycarboxylic acid such as those mentioned above, there are no residual COOH groups remaining that are not engaged in an ester bond.

The aliphatic hydroxycarboxylic acid ester is preferably chosen from esters of $C_2$ to $C_{16}$ aliphatic polyols, said polyols having reacted with an aliphatic hydroxy fatty acid bearing a saturated or unsaturated chain, comprising at least 12 carbon atoms. The fatty acid is preferably ricinoleic acid and the aliphatic hydroxycarboxylic acid ester is preferably hydrogenated castor oil.

Polycarboxylic Acid

The polycarboxylic acid comprises at least two COOH groups. It is advantageously a diacid dimer of unsaturated aliphatic carboxylic acid(s).

The polycarboxylic acid according to the invention is preferably aliphatic; it is advantageously an aliphatic dicarboxylic acid.

According to one embodiment, the polycarboxylic acid is a diacid dimer of unsaturated fatty acid(s), i.e. a dimer formed from at least one unsaturated fatty acid, for example from only one unsaturated fatty acid or from two different unsaturated fatty acids. The fatty acid is preferably monounsaturated or diunsaturated. The term "fatty acid" means an acid obtained by hydrolysis of fatty substances of plants or animal origin.

The diacid dimers of unsaturated fatty acid(s), or diacid dimer, are conventionally obtained by intermolecular dimerization reaction of at least one unsaturated fatty acid. Preferably, only one type of unsaturated fatty acid is dimerized.

The diacid dimers of unsaturated fatty acid(s) are especially obtained by dimerization of an unsaturated fatty acid especially of $C_8$ to $C_{34}$, especially of $C_{12}$ to $C_{22}$, in particular of $C_{16}$ to $C_{20}$ and more particularly of $C_{18}$.

As representatives of these unsaturated fatty acids, mention may be made especially of undecenoic acid, linderic acid, myristoleic acid, palmitoleic acid, oleic acid, linoleic acid, elaidinic acid, gadolenoic acid, eicosapentaenoic acid, docosahexaenoic acid, erucic acid, brassidic acid and arachidonic acid, and mixtures thereof.

The diacid dimer is preferably saturated, i.e. it does not comprise any carbon-carbon double bonds, and it is obtained by condensation of unsaturated fatty acid(s) optionally followed by hydrogenation, to convert any double bonds into single bonds.

The preferred diacid dimers of unsaturated fatty acid(s) are obtained by dimerization of linoleic acid, optionally followed by hydrogenation of the dimer thus obtained. The hydrogenated form may be partial or total, and may especially correspond to the saturated form, which is more oxidation-stable.

Diacid dimers and especially dilinoleic diacids whose stability toward oxidation has been improved by hydrogenation of the double bonds remaining after the dimerization reaction are also found commercially.

Any diacid dimer that is currently commercially available may be used in the present invention.

The polyester(s) may be present in the composition in accordance with the invention in an active material amount of between 0.1% and 30% by weight, preferably between 1% and 10% and even more preferentially between 2% and 8% by weight relative to the total weight of the composition.

According to a particular embodiment, the composition comprises the polyester(s) as defined previously in an active material amount at least equal to 10% by weight, preferably between 10% and 50% by weight and even more preferentially between 15% and 30% by weight relative to the total weight of the fatty phase.

Nonionic Cellulose Derivatives Comprising One or More Hydrophobic Substituents

The compositions in accordance with the invention comprise at least one nonionic cellulose derivative comprising one or more hydrophobic substituents containing from 8 to 30 carbon atoms.

For the purposes of the present invention, the term "cellulose derivative" means a compound comprising at least one cellobiose unit having the following structure:

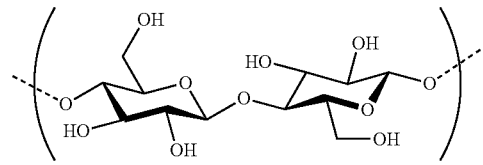

in which one or more hydroxyl groups may be substituted.

The nonionic cellulose derivative(s) bearing (a) hydrophobic substituent(s) in accordance with the present invention are amphiphilic polymers of associative nature. Specifically, they comprise hydrophilic units and hydrophobic units and are capable of reversibly interacting and combining with each other or with other molecules, in particular by virtue of the presence of their hydrophobic chains.

According to a particular embodiment, the cellulose derivative of the invention is a cellulose ether comprising one or more hydrophobic substituents comprising from 8 to 30 carbon atoms.

The nonionic cellulose derivative(s) bearing (a) hydrophobic substituent(s) in accordance with the present invention are generally prepared from water-soluble nonionic cellulose ethers, all or some of the reactive hydroxyl functions of which are substituted with one or more hydrophobic chains comprising from 8 to 30 carbon atoms, preferably from 10 to 22 carbon atoms and better still 16 carbon atoms. The reaction steps involved in the preparation of the cellulose derivatives of the invention are known to those skilled in the art.

The nonionic cellulose ethers chosen to prepare the nonionic cellulose derivatives bearing (a) hydrophobic substituent(s) according to the invention preferably have a degree of nonionic substitution, for example with methyl, hydroxyethyl or hydroxypropyl groups, which is sufficient to be water-soluble, i.e. to form a substantially clear solution when they are dissolved in water at 25° C. at a concentration of 1% by weight.

The nonionic cellulose ethers chosen to prepare the nonionic cellulose derivatives bearing (a) hydrophobic substituent(s) according to the invention preferentially have a relatively low number-average molar mass, of less than 800 000 g/mol, preferably ranging from 50 000 to 700 000 g/mol and more preferably ranging from 200 000 to 600 000 g/mol.

Preferably, the cellulose derivative of the invention is a hydroxyethylcellulose comprising one or more hydrophobic substituents comprising from 8 to 30 carbon atoms.

The nonionic cellulose derivatives used according to the invention are substituted with one or more linear, branched or cyclic, saturated or unsaturated, aliphatic or aromatic $C_8$-$C_{30}$ hydrocarbon-based chains, which may be attached to the cellulose ether substrate via an ether, ester or urethane bond, preferably an ether bond.

According to one embodiment, the hydrophobic substituent(s) used as substituents for the nonionic cellulose derivatives according to the present invention are $C_8$-$C_{30}$ and preferably $C_1$-$C_{22}$ alkyl, arylalkyl or alkylaryl groups.

Preferably, the hydrophobic substituent(s) according to the present invention are saturated alkyl chains.

According to a preferred embodiment, the hydrophobic substituent(s) according to the present invention are cetyl groups.

The nonionic cellulose derivatives bearing (a) hydrophobic substituent(s) according to the invention have a viscosity preferably between 100 and 100 000 mPa·s and preferably between 200 and 20 000 mPa·s, measured at 25° C. in a solution at 1% by weight of polymer in water, this viscosity being determined conventionally using a viscometer such as a Brookfield LVT machine at 6 rpm with a No. 3 spindle.

The degree of hydrophobic substitution of the hydrophilic nonionic cellulose derivatives used according to the invention preferentially ranges from 0.1% to 10% by weight, more preferentially from 0.1% to 1% by weight and particularly preferably from 0.4% to 0.8% by weight relative to the total weight of the polymer.

Among the nonionic cellulose derivatives bearing (a) hydrophobic substituent(s) that may be used in the compositions of the invention, mention may be made preferably of the cetyl hydroxyethylcelluloses sold under the names Natrosol Plus Grade 330 CS and Polysurf 67 CS (INCI: Cetyl hydroxyethylcellulose) by the company Ashland.

According to a particular embodiment, the active material concentration of the nonionic cellulose derivatives bearing (a) hydrophobic substituent(s) in the composition according to the invention ranges from 0.05% to 20% by weight, in particular from 0.25% to 10% by weight and preferentially from 0.5% to 3% by weight relative to the total weight of the composition.

The composition according to the second subject of the invention comprises at least one active agent chosen from C-glucoside derivatives, in particular C-beta-D-xylopyranoside-2-hydroxypropane, and cucurbic acid derivatives, such as the sodium salt of 3-hydroxy-2-pentylcyclopentyl) acetic acid.

C-Glycoside Derivatives

The C-glycoside derivative(s) advantageously have the property of exerting their hygroscopic effects on the skin and not in the cosmetic composition. Advantageously, a cosmetic composition comprising a C-glycoside derivative may exert a long-term care action, even after it has been removed from the tissues.

The C-glycoside derivative(s) that may be present in the composition in accordance with the invention are chosen from the compounds of general formula (I) below:

in which:
R denotes an unsubstituted linear $C_1$-$C_4$ and especially $C_1$-$C_2$ alkyl radical, in particular methyl;
S represents a monosaccharide chosen from D-glucose, D-xylose, N-acetyl-D-glucosamine and L-fucose, and in particular D-xylose;
X represents a group chosen from —CO—, —CH(OH)— and —CH(NH$_2$)— and preferentially a —CH(OH)— group;
and also the cosmetically acceptable salts thereof, solvates thereof such as hydrates, and optical isomers thereof.

As nonlimiting illustrations of C-glycoside derivatives that are more particularly suitable for use in the invention, mention may be made especially of the following derivatives:
C-beta-D-xylopyranoside-n-propan-2-one;
C-alpha-D-xylopyranoside-n-propan-2-one;
C-beta-D-xylopyranoside-2-hydroxypropane;
C-alpha-D-xylopyranoside-2-hydroxypropane;
1-(C-beta-D-glucopyranosyl)-2-hydroxypropane;
1-(C-alpha-D-glucopyranosyl)-2-hydroxpropane;
1-(C-beta-D-glucopyranosyl)-2-aminopropane;
1-(C-alpha-D-glucopyranosyl)-2-aminopropane;
3'-(acetamido-C-beta-D-glucopyranosyl)propan-2'-one;
3'-(acetamido-C-alpha-D-glucopyranosyl)propan-2'-one;
1-(acetamido-C-beta-D-glucopyranosyl)-2-hydroxypropane;
1-(acetamido-C-beta-D-glucopyranosyl)-2-aminopropane;
and also the cosmetically acceptable salts thereof, solvates thereof such as hydrates, and optical isomers thereof.

According to a particular embodiment, C-beta-D-xylopyranoside-2-hydroxypropane or C-alpha-D-xylopyranoside-2-hydroxypropane, and better still C-beta-D-xylopyranoside-2-hydroxypropane, may be advantageously used for the preparation of a composition according to the invention.

According to a particular embodiment, a C-glycoside derivative that is suitable for use in the invention may advantageously be hydroxypropyltetrahydropyrantriol, also known as C-beta-D-xylopyranoside-2-hydroxpropane, sold especially as a solution at 30% by weight in a water/propylene glycol mixture (60/40) under the name Mexoryl SBB® by Chimex. According to one embodiment, the C-glycoside derivative is in the form of a solution in which it is present in an amount of 30% by weight relative to the total weight of the solution, the remainder being a mixture of water and propylene glycol.

The salts of the C-glycoside derivatives that are suitable for use in the invention may comprise conventional physiologically acceptable salts of these compounds, such as those formed from organic or mineral acids. Examples that may be mentioned include the salts of mineral acids, such as sulfuric acid, hydrochloric acid, hydrobromic acid, hydroiodic acid, phosphoric acid and boric acid. Mention may also be made of the salts of organic acids, which may comprise one or more carboxylic, sulfonic or phosphonic acid groups. They may be linear, branched or cyclic aliphatic acids, or alternatively aromatic acids. These acids may also comprise one or more heteroatoms chosen from 0 and N, for example in the form of hydroxyl groups. Mention may be made especially of propionic acid, acetic acid, terephthalic acid, citric acid and tartaric acid.

The solvates that are acceptable for the compounds described above comprise conventional solvates such as those formed during the final step of preparation of said compounds due to the presence of solvents. Examples that may be mentioned include solvates due to the presence of water or of linear or branched alcohols, such as ethanol or isopropanol.

A C-glycoside derivative that is suitable for use in the invention may especially be obtained via the synthetic method described in document WO 02/051 828, the content of which is incorporated herein by reference.

According to one embodiment, the composition according to the invention comprises a C-glycoside derivative in an amount of between 0.03% and 30% by weight of active material (C-glycoside derivative) relative to the total weight of the composition, in particular between 0.03% and 10% by weight of active material relative to the total weight of the composition and more particularly between 0.05% and 5% by weight of active material relative to the total weight of the composition.

Cucurbic Acid Derivatives

The cucurbic acid derivative(s) that may be present in the composition in accordance with the invention are compounds chosen from those corresponding to formula (II) below:

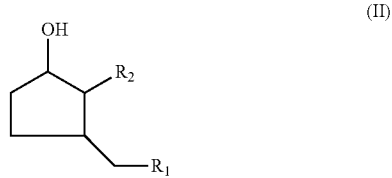

(II)

in which:

$R_1$ represents a radical COOR3, R3 denoting a hydrogen atom or a C1-C4 alkyl radical, optionally substituted with one or more hydroxyl groups;

$R_2$ represents a saturated or unsaturated linear hydrocarbon-based radical containing from 1 to 18 carbon atoms or a saturated or unsaturated branched or cyclic hydrocarbon-based radical containing from 3 to 18 carbon atoms;

and also the cosmetically acceptable salts thereof, solvates thereof such as hydrates, and optical isomers thereof.

Preferably, $R_1$ denotes a radical chosen from —COOH, —COOMe, —COO—CH2-CH3, —COO—CH2-CH(OH)—CH2OH, —COOCH2-CH2-CH2OH and —COOCH2-CH(OH)—CH3. Preferentially, $R_1$ denotes a —COOH radical.

Preferentially, $R_2$ denotes a saturated or unsaturated linear hydrocarbon-based radical, preferably containing from 2 to 7 carbon atoms. In particular, $R_2$ may be a pentyl, pentenyl, hexyl or heptyl radical.

According to one embodiment, the cucurbic acid derivative is chosen from 3-hydroxy-2-[(2Z)-2-pentenyl]cyclopentaneacetic acid and 3-hydroxy-2-pentyl-cyclopentaneacetic acid, and also the cosmetically acceptable salts thereof, solvates thereof such as hydrates, and optical isomers thereof. Preferably, the cucurbic acid derivative is chosen from 3-hydroxy-2-pentylcyclopentaneacetic acid, and also the cosmetically acceptable salts thereof, solvates thereof such as hydrates, and optical isomers thereof; this compound may especially be in the form of the sodium salt. An example that may be mentioned is the sodium salt of 3-hydroxy-2-pentylcyclopentaneacetic acid at 30% in a 70/30 water/dipropylene glycol mixture at neutral pH, sold under the name Mexoryl SBO® by the company Chimex.

The salts of the compounds that may be used according to the invention are in particular chosen from salts of alkali metals, for example sodium or potassium; salts of alkaline-earth metals, for example calcium, magnesium or strontium; metal salts, for example zinc, aluminum, manganese or copper; ammonium salts of formula $NH_4^+$; quaternary ammonium salts; salts of organic amines, for instance salts of methylamine, dimethylamine, trimethylamine, triethylamine, ethylamine, 2-hydroxyethylamine, bis(2-hydroxyethyhamine or tris(2-hydroxyethyhamine; lysine or arginine salts. Salts chosen from sodium, potassium, magnesium, strontium, copper, manganese and zinc salts are preferably used. The sodium salt is preferentially used.

The solvates that are acceptable for the compounds described above comprise conventional solvates such as those formed during the final step of preparation of said compounds due to the presence of solvents. Examples that may be mentioned include solvates due to the presence of water or of linear or branched alcohols, such as ethanol or isopropanol.

The cucurbic acid derivative(s) as defined previously may be present in the composition according to the invention in an active material content ranging from 0.01% to 15% by weight, preferably from 0.01% to 12% by weight and more particularly from 0.05% to 5% by weight, relative to the total weight of the composition.

Fatty Phase

The proportion of the fatty phase may range, for example, from 0.5% to 60% by weight, preferably from 5% to 40% by weight and even more preferentially from 10% to 35% by weight relative to the total weight of the composition.

This indicated amount comprises the content of polyesters as defined previously when the composition contains any. On the other hand, it does not comprise the content of lipophilic surfactants, when the composition contains these surfactants.

For the purposes of the invention, the fatty phase includes any fatty substance that is liquid at room temperature and atmospheric pressure, generally oils, or that is solid at room temperature and atmospheric pressure, like waxes, or any pasty compound, which are present in said composition, including the polyesters as defined previously.

The fatty phase of the compositions in accordance with the invention comprises at least one pasty fatty substance.

For the purposes of the present invention, the term "pasty fatty substance" means a lipophilic fatty compound that undergoes a reversible solid/liquid change in state, which has, in the solid state, an anisotropic crystalline arrangement and which comprises, at a temperature of 23° C., a liquid fraction and a solid fraction.

In other words, the starting melting point of the pasty fatty substance can be less than 23° C. The liquid fraction of the pasty fatty substance measured at 23° C. can represent from 9% to 97% by weight of the pasty fatty substance. This liquid fraction at 23° C. preferably represents between 15% and 85% and more preferably between 40% and 85% by weight.

Within the context of the invention, the melting point corresponds to the temperature of the most endothermic peak observed in thermal analysis (DSC) as described in the standard ISO 11357-3; 1999. The melting point of a pasty fatty substance may be measured using a differential scanning calorimeter (DSC), for example the calorimeter sold under the name MDSC 2920 by the company TA Instruments.

The measuring protocol is as follows:
A sample of 5 mg of pasty fatty substance placed in a crucible is subjected to a first temperature rise ranging from −20° C. to 100° C., at a heating rate of 10° C./minute, is then cooled from 100° C. to −20° C. at a cooling rate of 10° C./minute and is finally subjected to a second temperature rise ranging from −20° C. to 100° C. at a heating rate of 5° C./minute. During the second temperature rise, the variation in the difference in power absorbed by the empty crucible and by the crucible containing the sample of pasty fatty substance is measured as a function of the temperature. The melting point of the pasty fatty substance is the value of the temperature corresponding to the tip of the peak of the curve representing the variation in the difference in power absorbed as a function of the temperature.

The liquid fraction by weight of the pasty fatty substance at 23° C. is equal to the ratio of the enthalpy consumed at 23° C. to the enthalpy of the pasty fatty substance.

The enthalpy of fusion of the pasty fatty substance is the enthalpy consumed by the substance in order to pass from the solid state to the liquid state. The pasty fatty substance is said to be in the solid state when all of its mass is in crystalline solid form. The pasty fatty substance is said to be in the liquid state when all of its mass is in liquid form.

The enthalpy of fusion of the pasty fatty substance is equal to the area under the curve of the thermogram obtained using a differential scanning calorimeter (DSC), such as the calorimeter sold under the name MDSC 2920 by the company TA Instruments, with a temperature rise of 5° C. or 10° C. per minute, according to the standard ISO 11357-3:1999.

The enthalpy of fusion of the pasty fatty substance is the amount of energy required to make the pasty fatty substance change from the solid state to the liquid state. It is expressed in J/g. The enthalpy of fusion consumed at 23° C. is the amount of energy absorbed by the sample to change from the solid state to the state that it has at 23° C., formed from a liquid fraction and a solid fraction.

The liquid fraction of the pasty fatty substance measured at 32° C. preferably represents from 30% to 100% by weight of the pasty fatty substance, preferably from 50% to 100% and more preferably from 60% to 100% by weight of the pasty fatty substance. When the liquid fraction of the pasty fatty substance measured at 32° C. is equal to 100%, the temperature of the end of the melting range of the pasty fatty substance is less than or equal to 32° C.

The liquid fraction of the pasty fatty substance measured at 32° C. is equal to the ratio of the enthalpy of fusion consumed at 32° C. to the enthalpy of fusion of the pasty fatty substance. The enthalpy of fusion consumed at 32° C. is calculated in the same way as the enthalpy of fusion consumed at 23° C.

The pasty fatty substance may be chosen from synthetic fatty substances and fatty substances of plant origin. A pasty fatty substance may be obtained by synthesis from starting materials of plant origin.

The pasty fatty substance is advantageously chosen from:
lanolin and derivatives thereof,
  polyol ethers chosen from pentaerythrityl ethers of a polyalkylene glycol, fatty alkyl ethers of a sugar, and mixtures thereof, the pentaerythrityl ether of polyethylene glycol comprising 5 oxyethylene units (5 OE) (CTFA name: PEG-5 Pentaerythrityl Ether), polypropylene glycol pentaerythrityl ether comprising five oxypropylene (5 OP) units (CTFA name: PPG-5 Pentaerythrityl Ether) and mixtures thereof, and more especially the mixture PEG-5 Pentaerythrityl Ether, PPG-5 Pentaerythrityl Ether and soybean oil, sold under the name Lanolide by the company Vevy, which is a mixture in which the constituents are in a 46/46/8 weight ratio: 46% PEG-5 pentaerythrityl ether, 46% PPG-5 pentaerythrityl ether and 8% soybean oil,
polymeric or non-polymeric silicone compounds,
polymeric or non-polymeric fluoro compounds,
vinyl polymers, especially:
  olefin homopolymers and copolymers,
  hydrogenated diene homopolymers and copolymers,
  liposoluble polyethers resulting from polyetherification between one or more C2-C100 and preferably C2-050 diols,
esters,
and/or mixtures thereof.

The pasty fatty substance is preferably a polymer, especially a hydrocarbon-based polymer.

Among the liposoluble polyethers that are particularly preferred are copolymers of ethylene oxide and/or of propylene oxide with $C_6$-$C_{30}$ long-chain alkylene oxides, more preferably such that the weight ratio of the ethylene oxide and/or of the propylene oxide to the alkylene oxides in the copolymer is from 5:95 to 70:30. In this family, mention will be made especially of copolymers such as long-chain alkylene oxides arranged in blocks with an average molecular weight from 1000 to 10 000, for example a polyoxyethylene/polydodecyl glycol block copolymer such as the ethers of dodecanediol (22 mol) and of polyethylene glycol (45 OE) sold under the brand name Elfacos ST9 by Akzo Nobel.

Among the esters, the following are especially preferred:
esters of a glycerol oligomer, especially diglycerol esters, in particular condensates of adipic acid and of glycerol, for which some of the hydroxyl groups of the glycerols have reacted with a mixture of fatty acids such as stearic acid, capric acid, isostearic acid and 12-hydroxystearic acid, especially such as the product sold under the brand name Softisan 649 by the company Sasol,
the arachidyl propionate sold under the brand name Waxenol 801 by Alzo,
phytosterol esters,
fatty acid triglycerides and derivatives thereof,
pentaerythrityl esters,
esters of a diol dimer and of a diacid dimer, where appropriate esterified on their free alcohol or acid functional group(s) with acid or alcohol radicals, especially dimer dilinoleate esters; such esters may be chosen especially from the esters having the following INCI nomenclature: bis-behenyl/isostearyl/phytosteryl dimer dilinoleyl dimer dilinoleate (Plandool G), phytosteryl isostearyl dimer dilinoleate (LusoIan PI-DA, LusoIan PHY/IS-DA), phytosteryl/isostearyl/cetyl/stearyl/behenyl dimer dilinoleate (Plandool H or Plandool S), and mixtures thereof.

Other preferred pasty fatty substances that may also be mentioned include:

- mango butter, such as the product sold under the reference Lipex 203 by the company AarhusKarlshamn,
- hydrogenated soybean oil, hydrogenated copra oil, hydrogenated rapeseed oil, mixtures of hydrogenated vegetable oils such as the mixture of hydrogenated soybean, copra, palm and rapeseed vegetable oil, for example the mixture sold under the reference Akogel® by the company AarhusKarlshamn (INCI name: Hydrogenated Vegetable Oil),
- shea butter, in particular the product whose INCI name is *Butyrospermum parkii* Butter, such as the product sold under the reference Sheasoft® by the company AarhusKarlshamn,
- cocoa butter, in particular the product which is sold under the name CT Cocoa Butter Deodorized by the company Dutch Cocoa BV or the product which is sold under the name Beurre De Cacao NCB HD703 758 by the company Barry Callebaut,
- shorea butter, in particular the product which is sold under the name Dub Shorea T by the company Stéarineries Dubois,
- and mixtures thereof.

According to a particular embodiment of the invention, the composition comprises at least one pasty fatty substance chosen from the polyesters as defined previously.

The fatty phase of the compositions in accordance with the invention may also comprise at least one fatty substance chosen from solid fatty substances such as waxes and liquid fatty substances such as oils.

The waxes under consideration in the context of the present invention are generally lipophilic compounds that are solid and deformable or undeformable at room temperature (25° C.), with a solid/liquid reversible change of state, having a melting point of greater than or equal to 30° C., which may range up to 200° C. and especially up to 120° C.

By bringing one or more waxes, in accordance with the invention, to the liquid state (melting), it is possible to render them miscible with one or more oils and to form a macroscopically homogeneous wax(es)+oil(s) mixture, but on returning the temperature of said mixture to room temperature, recrystallization of the wax(es) in the oil(s) of the mixture is obtained. Within the context of the invention, the melting point corresponds to the temperature of the most endothermic peak observed in thermal analysis (DSC) as described in the standard ISO 11357-3; 1999. The melting point of the wax may be measured using a differential scanning calorimeter (DSC), for example the calorimeter sold under the name MDSC 2920 by the company TA Instruments.

The measuring protocol is as follows:

A sample of 5 mg of wax placed in a crucible is subjected to a first temperature rise ranging from −20° C. to 100° C., at a heating rate of 10° C./minute, then is cooled from 100° C. to −20° C. at a cooling rate of 10° C./minute and is finally subjected to a second temperature rise ranging from −20° C. to 100° C. at a heating rate of 5° C./minute. During the second temperature rise, the variation in the difference in power absorbed by the empty crucible and by the crucible containing the sample of wax is measured as a function of the temperature. The melting point of the compound is the temperature value corresponding to the top of the peak of the curve representing the variation in the difference in power absorbed as a function of the temperature.

The waxes that may be used in a composition according to the invention are chosen from waxes that are solid at room temperature, of animal, plant, mineral or synthetic origin, and mixtures thereof. They may be hydrocarbon-based, fluoro and/or silicone waxes.

Examples that may especially be mentioned include hydrocarbon-based waxes, such as natural beeswax (or bleached beeswax), synthetic beeswax, carnauba wax, rice bran wax, such as the product sold under the reference NC 1720 by the company Cera Rica Noda, candelilla wax, such as the product sold under the reference SP 75 G by the company Strahl & Pitsch, microcrystalline waxes, for instance the microcrystalline waxes of which the melting point is above 85° C., such as the products HI-MIC® 1070, 1080, 1090 and 3080 sold by the company Nippon Seiro, ceresins or ozokerites, for instance isoparaffins of which the melting point is below 40° C., such as the product EMW-0003 sold by the company Nippon Seiro, α-olefin oligomers, such as the Performa V® 825, 103 and 260 polymers sold by the company New Phase Technologies; ethylene/propylene copolymers, such as Performalene® EP 700, polyethylene waxes (preferably having a molecular weight of between 400 and 600), Fischer-Tropsch waxes, the sunflower seed wax sold by the company Koster Keunen under the reference sunflower wax.

Mention may also be made of silicone waxes, for instance alkyl or alkoxy dimethicones containing from 16 to 45 carbon atoms, and fluoro waxes.

According to a particular embodiment, the wax used in a composition in accordance with the invention has a melting point of greater than 35° C., better still greater than 40° C., or even greater than 45° C. or greater than 55° C.

The fatty phase of the compositions in accordance with the invention may also comprise at least one volatile or non-volatile oil.

The term "oil" means any fatty substance that is in liquid form at room temperature (25° C.) and at atmospheric pressure.

The volatile or non-volatile oils may be hydrocarbon-based oils, especially of animal or plant origin, synthetic oils, silicone oils or fluoro oils, or mixtures thereof.

For the purposes of the present invention, the term "silicone oil" means an oil comprising at least one silicon atom, and especially at least one Si—O group.

The term "hydrocarbon-based oil" means an oil mainly containing hydrogen and carbon atoms and possibly oxygen, nitrogen, sulfur and/or phosphorus atoms.

Non-Volatile Oils

For the purposes of the present invention, the term "non-volatile oil" means an oil with a vapor pressure of less than 0.13 Pa (0.01 mmHg).

The non-volatile oils may be chosen especially from non-volatile hydrocarbon-based oils, which may be fluorinated, and/or non-volatile silicone oils.

As non-volatile hydrocarbon-based oils that are suitable for use in the invention, mention may be made especially of:

- hydrocarbon-based oils of animal origin,
- hydrocarbon-based oils of plant origin such as phytostearyl esters, such as phytostearyl oleate, phytostearyl isostearate and lauroyl/octyldodecyl/phytostearyl glutamate, for example sold under the name Eldew PS203 by Ajinomoto, triglycerides consisting of fatty acid esters of glycerol, the fatty acids of which may have chain lengths ranging from $C_4$ to $C_{24}$, these chains possibly being linear or branched, and saturated or unsaturated; these oils are especially heptanoic or octanoic triglycerides, wheatgerm oil, sunflower oil, grapeseed oil, sesame oil, corn oil, apricot oil, castor oil, shea oil, avocado oil, olive oil, soybean oil, sweet almond oil, palm oil, rapeseed oil, cotton seed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion flower oil or musk rose oil; shea butter; or alternatively caprylic/capric acid triglycerides, for instance those sold by the company Stéarineries Dubois or those sold under the names Miglyol 810®, 812® and 818® by the company Dynamit Nobel; the refined vegetable perhydrosqualene sold under the name Fitoderm by the company Cognis;

hydrocarbon-based oils of mineral or synthetic origin, for instance:
  synthetic ethers having from 10 to 40 carbon atoms;
  linear or branched hydrocarbons of mineral or synthetic origin, such as petroleum jelly, polydecenes, hydrogenated polyisobutene such as Parleam, and squalane, and mixtures thereof, and in particular hydrogenated polyisobutene;
  synthetic esters, for instance oils of formula $R_1COOR_2$ in which $R_1$ represents a linear or branched fatty acid residue containing from 1 to 40 carbon atoms and $R_2$ represents a hydrocarbon-based chain that is especially branched, containing from 1 to 40 carbon atoms provided that $R_1+R_2 \geq 10$.

The esters may be chosen especially from fatty acid esters, for example:
  cetostearyl octanoate, isopropyl alcohol esters, such as isopropyl myristate or isopropyl palmitate, ethyl palmitate, 2-ethylhexyl palmitate, isopropyl stearate or isostearate, isostearyl isostearate, octyl stearate, hydroxylated esters, for instance isostearyl lactate, octyl hydroxystearate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate and palmitate, alkyl benzoate, polyethylene glycol diheptanoate, propylene glycol 2-diethylhexanoate, and mixtures thereof, $C_{12}$ to $C_{15}$ alcohol benzoates, hexyl laurate, neopentanoic acid esters, for instance isodecyl neopentanoate, isotridecyl neopentanoate, isostearyl neopentanoate and octyldodecyl neopentanoate, isononanoic acid esters, for instance isononyl isononanoate, isotridecyl isononanoate and octyl isononanoate, and hydroxylated esters, for instance isostearyl lactate and diisostearyl malate;
  polyol esters and pentaerythrityl esters, for instance dipentaerythrityl tetrahydroxystearate/tetraisostearate;
  esters of diol dimers and of diacid dimers, such as Lusplan DD-DA5® and Lusplan DD-DA7® sold by the company Nippon Fine Chemical and described in patent application FR 0302809;
  fatty alcohols that are liquid at room temperature, with a branched and/or unsaturated carbon-based chain containing from 12 to 26 carbon atoms, for instance 2-octyldodecanol, isostearyl alcohol, oleyl alcohol, 2-hexyldecanol, 2-butyloctanol and 2-undecylpentadecanol,
  higher fatty acids such as oleic acid, linoleic acid and linolenic acid, and mixtures thereof; and
  dialkyl carbonates, the two alkyl chains possibly being identical or different, such as the dicaprylyl carbonate sold under the name Cetiol CC® by Cognis;
  non-volatile silicone oils, for instance non-volatile polydimethylsiloxanes (PDMSs), polydimethylsiloxanes comprising alkyl or alkoxy groups that are pendent and/or at the end of a silicone chain, these groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, and dimethicones or phenyl trimethicones with a viscosity of less than or equal to 100 cSt, and mixtures thereof;
and mixtures thereof.

Volatile Oils

For the purposes of the present invention, the term "volatile oil" means an oil (or non-aqueous medium) that is capable of evaporating on contact with the skin in less than one hour, at room temperature and at atmospheric pressure. The volatile oil is a volatile cosmetic oil, which is liquid at room temperature, especially having a nonzero vapor pressure, at room temperature and atmospheric pressure, in particular having a vapor pressure ranging from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The volatile hydrocarbon-based oils may be chosen from hydrocarbon-based oils containing from 8 to 16 carbon atoms, and especially branched $C_8$-$C_{16}$ alkanes (also known as isoparaffins), for instance isododecane (also known as 2,2,4,4,6-pentamethylheptane), isodecane, isohexadecane and, for example, the oils sold under the trade names Isopars® or Permethyls®.

Volatile oils that may also be used include volatile silicones, for instance volatile linear or cyclic silicone oils, especially those with a viscosity $\leq 8$ centistokes ($8 \times 10^{-6}$ m$^2$/s), and especially containing from 2 to 10 silicon atoms and in particular from 2 to 7 silicon atoms, these silicones optionally comprising alkyl or alkoxy groups containing from 1 to 10 carbon atoms. As volatile silicone oils that may be used in the invention, mention may be made especially of dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Volatile fluoro oils such as nonafluoromethoxybutane or perfluoromethyl-cyclopentane, and mixtures thereof, may also be used.

It is also possible to use a mixture of the oils mentioned above.

The other fatty substances that may be present in the fatty phase are, for example, fatty acids comprising from 8 to 30 carbon atoms, for instance stearic acid, lauric acid or palmitic acid; fatty alcohols comprising from 8 to 30 carbon atoms, for instance stearyl alcohol or cetyl alcohol and mixtures thereof (cetearyl alcohol).

According to a particular embodiment, the fatty phase of the compositions in accordance with the invention comprises at least one pasty fatty substance chosen from polyesters resulting from the esterification, with a polycarboxylic acid, of an aliphatic hydroxycarboxylic acid ester comprising at least two hydroxyl groups as defined previously and at least one additional fatty substance other than said polyesters. Preferably, this additional fatty substance is chosen from hydrocarbon-based oils of plant origin and volatile oils as defined above. According to a particular embodiment, the composition comprises the polyester(s) as defined previously in an active material amount at least equal to 10% by weight, preferably between 10% and 50% by weight and even more preferentially between 15% and 30% by weight relative to the total weight of the fatty phase.

The fatty phase may also contain other compounds dissolved in the oils, such as gelling agents and/or structuring agents.

These compounds may be chosen especially from gums, such as silicone gums (dimethiconol); silicone resins, such as trifluoromethyl(C1-C4 alkyl) dimethicone and trifluoropropyl dimethicone, and silicone elastomers, for instance the products sold under the KSG names by the company Shin-Etsu, under the name Trefil by the company Dow Corning or under the Gransil names by the company Grant Industries; and mixtures thereof.

These fatty substances may be chosen in a varied manner by a person skilled in the art so as to prepare a composition having the desired properties, for example in terms of consistency or texture.

Aqueous Phase

The aqueous phase of the composition according to the invention comprises at least water. Depending on the galenical form of the composition, the amount of aqueous phase may range from 10% to 95% by weight, preferably from 20% to 90% by weight and better still from 30% to 85% by weight relative to the total weight of the composition. This amount depends on the galenical form of the composition desired. The amount of water may represent all or a portion of the aqueous phase and it is generally at least 35% by weight relative to the total weight of the composition.

The aqueous phase may comprise at least one hydrophilic solvent, for instance substantially linear or branched lower monoalcohols containing from 1 to 8 carbon atoms, such as ethanol, propanol, butanol, isopropanol or isobutanol; polyols, such as propylene glycol, isoprene glycol, butylene glycol, glycerol, sorbitol, polyethylene glycols and derivatives thereof; and mixtures thereof.

According to a particular embodiment of the invention, the composition is free of emulsifying surfactant or contains less than 3% by weight relative to the total weight of the composition of emulsifying surfactant.

When an emulsifying surfactant is added, it may be chosen, alone or as a mixture, from the hydrophilic and lipophilic emulsifying surfactants commonly used in cosmetics. The nature of the surfactant(s) will be chosen according to the sense of the emulsion: direct (O/W) or inverse (W/O).

In a known manner, all the compositions of the invention may comprise one or more of the adjuvants that are common in cosmetics and dermatology: hydrophilic or lipophilic gelling agents and/or thickeners; moisturizers; emollients; hydrophilic or lipophilic active agents; free-radical scavengers; sequestrants; antioxidants; preserving agents; basifying or acidifying agents; fragrances; film-forming agents; and mixtures thereof.

The amounts of these various adjuvants are those conventionally used in the fields under consideration. In particular, the amounts of adjuvants vary according to the desired objective and are those conventionally used in the fields under consideration, for example from 0.1% to 20%, and preferably from 0.5% to 10% of the total weight of the composition.

Fillers and/or Pigments

According to a particular embodiment, the composition in accordance with the invention comprises at least one filler, preferably with an optical effect, and/or at least one pigment. For the purposes of the present invention, the term "filler with an optical effect" means a filler which makes it possible to obtain immediate effects on the skin, such as a matt, unifying, soft-focus (transparency, matt or hazy effect) or lightening effect.

As fillers that may be used in the composition of the invention, examples that may be mentioned include silicas such as the polymer with the INCI name Methylsilanol/Silicate Crosspolymer sold under the name NLK 506 by the company Takemoto Oil & Fat; silica such as the silica microspheres sold under the name SB 700 by the company Miyoshi Kasei or under the names Sunsphere H-33, Sunsphere H-51 and Solesphere H-33 by the company AGC Si-Tech; kaolin; talc; boron nitride; titanium oxides, for instance Microtitanium Dioxide MT-100 TV (INCI name: Titanium Dioxide (and) Aluminum Hydroxide (and) Stearic Acid) sold by the company Tayca, and Microtitanium Dioxide MT-100AQ (INCI name: Titanium Dioxide (and) Silica (and) Aluminum Hydroxide (and) Alginic Acid) sold by the company Tayca; bismuth oxychloride, such as the product sold under the name Ronaflair LF 2000 by the company Merck; spherical organic powders, fibers; and mixtures thereof. Examples of organic spherical powders that may be mentioned include polyamide powders and especially Nylon® powders such as Nylon-1 or Polyamide 12, sold under the name Orgasol by the company Atochem; polyethylene powders; Teflon®; microspheres based on acrylic copolymers, such as those made of ethylene glycol dimethacrylate/lauryl methacrylate copolymer, sold by the company Dow Corning under the name Polytrap; expanded powders such as hollow microspheres and especially the microspheres sold under the name Expancel by the company Kemanord Plast or under the name Micropearl F 80 ED by the company Matsumoto; silicone resin microbeads such as those sold under the name Tospearl by the company Toshiba Silicone; polymethyl methacrylate microspheres, sold under the name Microsphere M-100 by the company Matsumoto or under the name Covabead LH85 by the company Wackherr; ethylene acrylate copolymer powders, such as those sold under the name Flobeads by the company Sumitomo Seika Chemicals; powders of natural organic materials such as cellulose powders, especially the product sold under the name Cellulobeads D-10 by the company Daito Kasei Kogyo, starch powders, especially of corn starch, wheat starch or rice starch, which may or may not be crosslinked, such as the starch powders crosslinked with octenyl succinate anhydride, sold under the name Dry-Flo by the company National Starch or starch derivatives such as the crosslinked sodium carboxymethylstarch (potato) sold under the name Glycolys by the company Roquette. Examples of fibers that may be mentioned include polyamide fibers, such as in particular Nylon 6 (or Polyamide 6) (INCI name: Nylon 6) fibers, Nylon 6,6 (or Polyamide 66) (INCI name: Nylon 66) fibers, or such as poly-p-phenyleneterephthamide fibers; and mixtures thereof.

The filler(s) that may be used in the context of the invention may also be chosen from silica aerogel particles such as those described in patent applications WO 2012/084 780 and WO 2012/084 781.

The term "pigments" should be understood as meaning white or colored, mineral or organic particles that are insoluble in an aqueous solution, which are intended to color and/or opacify the resulting composition.

As mineral pigments that may be used in the invention, mention may be made of titanium oxides, zirconium oxides or cerium oxides, and also zinc oxides, iron oxides or chromium oxides, ferric blue, manganese violet, ultramarine blue and chromium hydrate. Preferably, the composition of the invention comprises at least titanium oxides and iron oxides. Among the organic pigments that may be used in the invention, mention may be made of carbon black, pigments of D&C type, lakes based on cochineal carmine or on barium, strontium, calcium or aluminum, or alternatively the diketopyrrolopyrroles (DPPs) described in documents EP-A-542 669, EP-A-787 730, EP-A-787 731 and WO-A-96/08537.

According to a particular embodiment of the invention, the composition comprises at least one filler, preferably with an optical effect. Preferably, these fillers are chosen from boron nitride, cellulose beads, bismuth oxychloride and silicas.

The fillers and/or pigments may be present in amounts ranging from 0 to 20% by weight, preferably from 0.2% to 10% by weight and even more preferentially from 0.5% to 5% by weight relative to the total weight of the composition.

Active Agents

The compositions in accordance with the invention may comprise at least one active agent chosen from C-glucoside derivatives, in particular C-beta-D-xylopyranoside-2-hydroxypropane, and cucurbic acid derivatives, such as the sodium salt of 3-hydroxy-2-pentylcyclopentyl) acetic acid, such as those defined previously.

The compositions in accordance with the invention may also comprise one or more active agents different from the active agents chosen from C-glucoside derivatives, in particular C-beta-D-xylopyranoside-2-hydroxpropane, and cucurbic acid derivatives, especially the sodium salt of 3-hydroxy-2-pentylcyclopentyl) acetic acid, such as those defined previously. Nonlimiting examples of active agents that may be mentioned include ascorbic acid and derivatives thereof such as 5,6-di-O-dimethylsilyl ascorbate (sold by the company Exsymol under the reference PRO-AA), the potassium salt of dl-alpha-tocopheryl-2l-ascorbyl phosphate (sold by the company Senju Pharmaceutical under the reference Sepivital EPC), magnesium ascorbyl phosphate, sodium ascorbyl phosphate (sold by the company Roche under the reference Stay-C 50); phloroglucinol; enzymes; and mixtures thereof. According to a preferred embodiment of the invention, ascorbic acid is used among the oxidation-sensitive hydrophilic active agents. The ascorbic acid may be of any nature. Thus, it may be of natural origin in powder form or in the form of orange juice, preferably orange juice concentrate. It may also be of synthetic origin, preferably in powder form.

As other active agents that may be used in the composition of the invention, examples that may be mentioned include moisturizers, such as protein hydrolyzates and polyols, for instance glycerol, glycols, for instance polyethylene glycols; natural extracts; anti-inflammatories; oligomeric proanthocyanidins; vitamins such as vitamin A (retinol), vitamin E (tocopherol), vitamin B5 (panthenol), vitamin B3 (niacinamide), derivatives of these vitamins (especially esters) and mixtures thereof; caffeine; depigmenting agents such as kojic acid, hydroquinone and caffeic acid; salicylic acid and derivatives thereof; alpha-hydroxy acids, such as lactic acid and glycolic acid and derivatives thereof; retinoids, such as carotenoids and vitamin A derivatives; hydrocortisone; melatonin; extracts of algae, of fungi, of plants, of yeasts, of bacteria; steroids; antibacterial active agents, such as 2,4,4'-trichloro-2'-hydroxydiphenyl ether (or triclosan), 3,4,4'-trichlorocarbanilide (or triclocarban) and the acids indicated above, and especially salicylic acid and derivatives thereof; matt-effect agents, for instance fibers; tensioning agents; and mixtures thereof.

Needless to say, a person skilled in the art will take care to select the optional adjuvant(s) added to the composition according to the invention such that the advantageous properties intrinsically associated with the composition in accordance with the invention are not, or are not substantially, adversely affected by the envisaged addition.

The composition according to the invention is in the form of an emulsion. According to a particular embodiment of the invention, the composition is in the form of an emulsion of oil-in-water type or in the form of an emulsion of water-in-oil type. Preferably, it is in the form of an emulsion of oil-in-water type.

The composition according to the invention may be of semi-liquid consistency, for example of the milk type, obtained by dispersing a fatty phase in an aqueous phase, or suspensions or emulsions of soft, semi-solid or solid consistency of the cream or balm type. These compositions are prepared according to the usual methods.

In addition, the composition in accordance with the invention may be more or less thick and may have the appearance of a white or colored cream, a liquid to thick cream, an ointment, a milk, a serum, a paste, a butter or a mousse.

The composition preferably has a skin-friendly pH which generally ranges from 3 to 8 and preferably from 4 to 7.

The examples that follow will allow the invention to be understood more clearly, without, however, being limiting in nature. The starting materials are referred to by their INCI names. The amounts indicated are given as weight percentages of starting material, unless otherwise mentioned.

EXAMPLES

Comparative Examples 1 to 3

Oil-in-Water Emulsions

Compositions A, B and C below were prepared.

| Composition | A (invention) | B (prior art) | C (prior art) |
|---|---|---|---|
| PHASE A | | | |
| Aqua | qs 100 | qs 100 | qs 100 |
| Preserving agent(s) | qs | qs | qs |
| Glycerol | 7 | 7 | 7 |
| PHASE B | | | |
| Cetyl hydroxyethylcellulose (and) sodium nitrate (and) silica (and) polysorbate 60 (and) sodium acetate (Polysurf 67 CS from Ashland) | 1.2 | — | 1.2 |
| Hydroxyethylcellulose (Natrosol 250 HHR PC from Ashland) | — | 1.2 | — |
| PHASE C | | | |
| Hydrogenated castor oil dimer dilinoleate (Risocast DA-L from Kokyu Alcohol Kogyo) | 6 | 6 | — |
| Paraffinum liquidum (and) cera microcristallina (and) paraffin (Vaseline Blanche Codex 236 from Aiglon) | — | — | 6 |
| Dicaprylyl ether (Cetiol OE from Cognis) | 20 | 20 | 20 |

Procedure:

Once the preserving system has been dissolved in water+glycerol mixture (at the necessary temperature), add phase B to phase A with stirring using a Rayneri blender until the gel is homogeneous. Homogenize phase C (at the temperature necessary to have a homogeneous liquid phase). When the mixtures of phases (A+B) and C are homogeneous, form the emulsion in a conventional manner by adding phase C to phase (A+B) with vigorous stirring. Homogenize until a smooth cream is obtained.

For each of the compositions thus obtained, the immediate stability at room temperature and the stability after 2 months of storage under various temperature conditions: 4° C., room temperature (RT), 45° C., are evaluated.

Stabilities:

|  | Emulsion A (invention) | Emulsion B (prior art) | Emulsion C (prior art) |
|---|---|---|---|
| Results at T0 | smooth, fine emulsion | Unstable emulsion | Fragile emulsion which breaks after 2 weeks of storage |
| After 2 months at RT | Idem T0 Good stability | / | / |
| After 2 months at 4° C. | Idem T0 Good stability | / | / |
| After 2 months at 45° C. | Idem T0 | / | / |

Cosmetic/Sensory Properties:

|  | Emulsion A (invention) | Emulsion B (prior art) | Emulsion C (prior art) |
|---|---|---|---|
| Cosmetic properties | Soft, smooth, homogeneous, shiny, leaves the skin soft, nourished and soothed after application | After forced homogenization: runny, heterogeneous, gelatinous | Emulsion heavy and sticky on application, leaves the skin tacky and shiny |

Example 4

Refatting Nutrient Cream

Composition D below was prepared:

| Composition | D |
|---|---|
| PHASE A | |
| Aqua | qs 100 |
| Preserving agent(s) | qs |
| Glycerol | 7 |
| PHASE B | |
| Cetyl hydroxyethylcellulose (and) sodium nitrate (and) silica (and) polysorbate 60 (and) sodium acetate (Polysurf 67 CS from Ashland) | 1.2 |
| PHASE C | |
| Hydrogenated castor oil dimer dilinoleate (Risocast DA-H from Kokyu Alcohol Kogyo) | 6 |
| Dicaprylyl ether (Cetiol OE from Cognis) | 8 |
| *Simmondsia chinensis* oil | 7 |
| Hydrogenated polyisobutene (Parleam from NOF Corporation) | 5 |

Procedure:

Once the preserving system has been dissolved in water+glycerol mixture (at the necessary temperature), add phase B to phase A with stirring using a Rayneri blender until the gel is homogeneous. Homogenize phase C (at the temperature necessary to have a homogeneous liquid phase). When the mixtures of phases (A+B) and C are homogeneous, form the emulsion in a conventional manner by adding phase C to phase (A+B) with vigorous stirring. Homogenize until a smooth cream is obtained.

Example 5

Moisturizinq Milk

Composition E below was prepared:

| Composition | E |
|---|---|
| PHASE A | |
| Aqua | qs 100 |
| Preserving agent(s) | qs |
| Glycerol | 10 |
| PHASE B | |
| Cetyl hydroxyethylcellulose (and) sodium nitrate (and) silica (and) polysorbate 60 (and) sodium acetate (Polysurf 67 CS from Ashland) | 0.6 |
| PHASE C | |
| Hydrogenated castor oil dimer dilinoleate (Risocast DA-H from Kokyu Alcohol Kogyo) | 6 |
| Dicaprylyl ether (Cetiol OE from Cognis) | 10 |

Procedure:

Once the preserving system has been dissolved in water+glycerol mixture (at the necessary temperature), add phase B to phase A with stirring using a Rayneri blender until the gel is homogeneous. Homogenize phase C (at the temperature necessary to have a homogeneous liquid phase). When the mixtures of phases (A+B) and C are homogeneous, form the emulsion in a conventional manner by adding phase C to phase (A+B) with vigorous stirring. Homogenize until a smooth cream is obtained.

Example 6

Nutrient Cream with Immediate Effects

Composition F below was prepared:

| Composition | F |
|---|---|
| PHASE A | |
| Aqua | qs 100 |
| Preserving agent(s) | qs |
| Glycerol | 7 |
| PHASE B | |
| Cetyl hydroxyethylcellulose (and) sodium nitrate (and) silica (and) polysorbate 60 (and) sodium acetate (Polysurf 67 CS from Ashland) | 1.2 |
| PHASE C | |
| Hydrogenated castor oil dimer dilinoleate (Risocast DA-H from Kokyu Alcohol Kogyo) | 6 |
| Dicaprylyl ether (Cetiol OE from Cognis) | 8 |

-continued

| Composition | F |
|---|---|
| *Simmondsia chinensis* oil | 7 |
| Hydrogenated polyisobutene (Parleam from NOF Corporation) | 5 |
| PHASE D | |
| Boron nitride (Softouch Boron nitride Powder CC6058 from Momentive Performance Materials) | 2 |
| Cellulose (Cellulobeads D-10 from Daito Kasei Kogyo) | 2 |

Procedure:

Once the preserving system has been dissolved in water+glycerol mixture (at the necessary temperature), add phase B to phase A with stirring using a Rayneri blender until the gel is homogeneous. Homogenize phase C (at the temperature necessary to have a homogeneous liquid phase). When the mixtures of phases (A+B) and C are homogeneous, form the emulsion in a conventional manner by adding phase C to phase (A+B) with vigorous stirring. Homogenize until a smooth cream is obtained. At room temperature, add phase D.

A cream that is soft and fresh on application is obtained. After penetration of the cream, the skin is nourished, comfortable and has a smooth, matt appearance.

Example 7

The following compositions were prepared.

| | Composition A (comparative) | Composition B (invention) |
|---|---|---|
| Phase A | | |
| Hydroxypropyltetrahydropyrantriol (C-beta-D-xylopyranoside-2-hydroxypropane as a 30% solution in a 60/40 water/1,2-propanediol mixture: Mexoryl SBB ® from Chimex) | — | 3% AM |
| Preserving agent(s) | qs | qs |
| Water | qs | qs |
| Glycerol | 5 | 5 |
| PHASE B | | |
| Cetyl hydroxyethylcellulose (and) sodium nitrate (and) silica (and) polysorbate 60 (and) sodium acetate (Polysurf 67 CS from Ashland) | 1.22 | 1.22 |
| PHASE C | | |
| Caprylic/capric triglyceride | 3 | 3 |
| *Simmondsia chinensis* (jojoba) seed oil | 5 | 5 |
| Cetyl Alcohol | 2 | 2 |
| Hydrogenated castor oil dimer dilinoleate (Risocast DA-L from Kokyu Alcohol Kogyo) | 6 | 6 |
| Dicaprylyl ether (Cetiol OE from Cognis) | 11 | 11 |

Procedure:

Once the preserving system has been dissolved in water+glycerol mixture, add phase B to phase A with stirring using a Rayneri blender until the gel is homogeneous. Homogenize phase C (at the temperature necessary to have a homogeneous liquid phase). When the mixtures of phases (A+B) and C are homogeneous, form the emulsion in a conventional manner by adding phase C to phase (A+B) with vigorous stirring. Homogenize until a smooth cream is obtained.

Sensory Evaluation:

For each of the compositions A and B, the cosmetic properties were evaluated according to the following protocol.

The cosmetic properties on application are evaluated, monadically, by a panel of experts trained in the description of care products. The sensory evaluation of the care products by this panel is performed as follows: the products are packaged in opaque jars or pump-action bottles depending on the viscosity of the products. Within the same session, the samples are presented in random order to each panellist. 15 experts evaluated:

- the glidance (the opposite effect to the coarse effect which induces difficulty in application) in the following manner: on a hand precleaned with water and liquid soap and wiped dry with a tissue, 0.05 ml of product is applied to the top half of the hand (five cycles with the index and middle fingers). The product is evaluated during the five passes, and 2 minutes after application. The descriptor "glidance" is defined as being the ease of application of the product, its ability to cover a defined area and the capacity of the product not to drag on the skin during application. The descriptors are evaluated on a scale at five levels: None, Sparingly, Moderately, Quite, Very.
- the fluffing capacity: The products are evaluated on normal to combination skin. For each product, the experts evaluate (according to a standardized gesture) the fluffing capacity of the product during application, and then after application and 2 minutes of drying, according to a specific fluffing gesture (to-and-fro movements with the back of the hand over the cheek). Fluffing is defined as the presence of particles. The amount of particles may be "Low", "Moderate" or "High".
- the tacky effect during and after application. The descriptors are evaluated on a scale at five levels: None, Sparingly, Moderately, Quite, Very.

Results obtained on a panel of 15 experts:

| Formulation | A | B (invention) |
|---|---|---|
| Glidant effect | 3/15: quite<br>12/15: very | 2/15: quite<br>13/15: very |
| Fluffing capacity | Low (13/15)<br>Moderate (2/15) | Low (12/15)<br>Moderate (3/15) |
| The tacky effect | Sparingly (11/15)<br>None (4/15) | Sparingly (10/15)<br>None (5/15) |

The comparative evaluation of these two formulations indicates that, by means of the use of a combination of a pasty fatty substance with a hydrophobic-modified cellulose, pleasant textures may be obtained, even though they have a high concentration of active agents.

Example 8

The following compositions were prepared.

|  | Composition C (invention) | Composition D (comparative) | Composition E (comparative) |
|---|---|---|---|
| Phase A | | | |
| Water | qs for 100% | qs for 100% | qs for 100% |
| Preserving agent(s) | qs | qs | qs |
| Glycerol | 7 | 7 | 7 |
| Hydroxypropyltetrahydropyrantriol (C-beta-D-xylopyranoside-2-hydroxypropane as a 30% solution in a 60/40 water/1,2-propanediol mixture: Mexoryl SBB ® from Chimex) | 3% AM | 3% AM | 3% AM |
| Phase B | | | |
| Cetyl hydroxyethylcellulose (and) sodium nitrate (and) silica (and) polysorbate 60 (and) sodium acetate (Polysurf 67 CS from Ashland) | 1.2 | 1.2 | — |
| Phase C | | | |
| Hydrogenated castor oil dimer dilinoleate (Risocast DA-L from Kokyu Alcohol Kogyo) | 6 | — | 6 |
| Glyceryl stearate (and) PEG-100 stearate (Arlacel 165 from Croda) | — | — | 2.5 |
| *Simmondsia chinensis* (jojoba) seed oil | 5 | 5 | 5 |
| Dicaprylyl ether (Cetiol OE from Cognis) | 15 | 21 | 15 |

Procedure:

Once the preserving system has been dissolved in water (at the necessary temperature), add phase B to phase A with stirring using a Rayneri blender until the gel is homogeneous. Homogenize phase C (at the temperature necessary to have a homogeneous liquid phase). When the mixtures (A+B) and C are homogeneous, form the emulsion in a conventional manner by adding C to (A+B) with vigorous stirring. Homogenize until a smooth cream is obtained.

On the same evaluation protocol defined in Example 1, the results obtained on a panel of 15 experts are presented in the table below.

| Formulation | A (invention) | Emulsion B | Emulsion C |
|---|---|---|---|
| Glidant effect | 2/15: quite 13/15: very | 4/15: none 11/15: sparingly | 10/15: none 5/15: sparingly |
| Fluffing capacity | Low (12/15) Moderate (3/15) | High (11/15) Moderate (4/15) | High (13/15) Moderate (2/15) |
| The tacky effect | Sparingly (10/15) None (5/15) | Very (8/15) Quite (7/15) | Very (10/15) Quite (5/15) |

The comparative evaluation of these three formulations indicates that the formulation according to the invention (formulation A) is less tacky, less coarse and produces little fluffing when compared with comparative formulations B and C.

Example 9

The following compositions were prepared.

|  | Emulsion A (comparative) | Emulsion B (invention) |
|---|---|---|
| PHASE A | | |
| Water | qs 100% | qs 100% |
| Preserving agent(s) | qs | qs |
| Glycerol | 7% | 7% |
| Sodium tetrahydrojasmonate (3-hydroxy-2-pentylcyclopentyl)acetic acid, sodium salt, at 30% in a 70/30 water/dipropylene glycol mixture at neutral pH: Mexoryl SBO ® from Chimex) | — | 6.25% (i.e. 2% AM) |
| PHASE B | | |
| Cetyl hydroxyethylcellulose (and) sodium nitrate (and) silica (and) polysorbate 60 (and) sodium acetate (Polysurf 67 CS from Ashland) | 1.2 | 1.2 |
| PHASE C | | |
| Hydrogenated castor oil dimer dilinoleate (Risocast DA-L from Kokyu Alcohol Kogyo) | 6 | 6 |
| *Simmondsia chinensis* (jojoba) seed oil | 5 | 5 |
| Dicaprylyl ether (Cetiol OE from Cognis) | 15 | 15 |

Procedure:

Once the preserving system has been dissolved in water+glycerol mixture, add phase B to phase A with stirring using a Rayneri blender until the gel is homogeneous. Homogenize phase C (at the temperature necessary to have a homogeneous liquid phase). When the mixtures of phases (A+B) and C are homogeneous, form the emulsion in a conventional manner by adding phase C to phase (A+B) with vigorous stirring. Homogenize until a smooth cream is obtained.

On the same evaluation protocol defined in Example 1, the results obtained on a panel of 15 experts are given in the table below.

| Formulation | A | B (invention) |
|---|---|---|
| Glidant effect | 4/15: quite<br>11/15: very | 3/15: quite<br>12/15: very |
| Fluffing capacity | Low (12/15)<br>Moderate (3/15) | Low (12/15)<br>Moderate (3/15) |
| The tacky effect | Sparingly (11/15)<br>None (4/15) | Sparingly (12/15)<br>None (3/15) |

The comparative evaluation of these two formulations indicates that they have very similar cosmetic qualities. The addition of the cucurbic acid derivative, even at high content, does not affect the cosmetic qualities of the composition.

Example 10

The following compositions were prepared.

|  | Emulsion A (invention) | Emulsion B (comparative) | Emulsion C (comparative) |
|---|---|---|---|
| PHASE A | | | |
| Water | qs 100% | qs 100% | qs 100% |
| Preserving agent(s) | qs | qs | qs |
| Glycerol | 7% | 7% | 7% |
| Sodium tetrahydrojasmonate (3-hydroxy-2-pentylcyclopentyl) acetic acid, sodium salt, at 30% in a 70/30 water/dipropylene glycol mixture at neutral pH: Mexoryl SBO ® from Chimex) | 6.25%<br>(2% AM) | 6.25%<br>(2% AM) | 6.25%<br>(2% AM) |
| PHASE B | | | |
| Cetyl hydroxyethylcellulose (and) sodium nitrate (and) silica (and) polysorbate 60 (and) sodium acetate (Polysurf 67 CS from Ashland) | 1.2 | 1.2 | — |
| PHASE C | | | |
| Glyceryl stearate (and) PEG-100 stearate (Arlacel 165 from Croda) | — | — | 2.5 |
| Hydrogenated castor oil dimer dilinoleate (Risocast DA-L from Kokyu Alcohol Kogyo) | 6 | — | 6 |
| *Simmondsia chinensis* (jojoba) seed oil | 5 | 5 | 5 |
| Dicaprylyl ether (Cetiol OE from Cognis) | 15 | 21 | 15 |

Procedure:

Once the preserving system has been dissolved in water+glycerol mixture, add phase B to phase A with stirring using a Rayneri blender until the gel is homogeneous. Homogenize phase C (at the temperature necessary to have a homogeneous liquid phase). When the mixtures of phases (A+B) and C are homogeneous, form the emulsion in a conventional manner by adding phase C to phase (A+B) with vigorous stirring. Homogenize until a smooth cream is obtained.

On the same evaluation protocol defined in Example 1, the results obtained on a panel of 15 experts are given in the table below.

| Formulation | A (invention) | B (comparative) | C (comparative) |
|---|---|---|---|
| Glidant effect | 3/15: quite<br>12/15: very | 4/15: none<br>11/15: sparingly | 10/15: none<br>5/15: sparingly |
| Fluffing capacity | Low (12/15)<br>Moderate (3/15) | High (11/15)<br>Moderate (4/15) | High (13/15)<br>Moderate (2/15) |
| The tacky effect | Sparingly (12/15)<br>None (3/15) | Very (13/15)<br>Quite (2/15) | Very (10/15)<br>Quite (5/15) |

The comparative evaluation of these three formulations indicates that the formulation according to the invention (formulation A) is less tacky, less coarse and produces little fluffing when compared with formulations B and C.

The invention claimed is:

1. A composition in the form of an emulsion comprising 0.1% and 30% by weight relative to the total weight of the composition of hydrogenated castor oil dimer dilinoleate, at least one nonionic cellulose derivative comprising one or more hydrophobic substituents containing from 8 to 30 carbon atoms, and between 0.03% and 30% by weight relative to the total weight of the composition of C-beta-D-xylopyranoside-2-hydroxypropane, wherein the composition comprises from 0.5% to 60% by weight relative to the total weight of the composition of a fatty phase and less than 3% by weight of an emulsifying surfactant other than the at least hydrogenated castor oil dimer dilinoleate in the composition.

2. The composition as claimed in claim 1, wherein the nonionic cellulose derivative is a hydroxyethylcellulose substituted with one or more hydrophobic substituents comprising from 8 to 30 carbon atoms.

3. The composition as claimed in claim 1, wherein the at least one nonionic cellulose derivative has a degree of hydrophobic substitution ranges from 0.1% to 10% by weight relative to the total weight of the at least one nonionic cellulose derivative.

4. The composition as claimed in claim 1, wherein the concentration of the at least one nonionic cellulose derivative comprising one or more hydrophobic substituents in the composition ranges from 0.05% to 20% by weight relative to the total weight of the composition.

5. The composition as claimed in claim 1, wherein the hydrogenated castor oil dimer dilinoleate is present in an amount at least equal to 10% by weight relative to the total weight of the fatty phase.

6. The composition as claimed in claim 1, also comprising at least one filler.

7. The composition as claimed in claim 1, which is a cosmetic composition.

8. A cosmetic process for treating a keratin material, in which a composition as defined in claim 1 is applied to the keratin material.

9. The composition as claimed in claim 1, wherein the amount of the fatty phase is 5% to 40% by weight relative to the total weight of the composition.

10. The composition as claimed in claim 1, wherein the amount of the fatty phase is 10% to 35% by weight relative to the total weight of the composition.

* * * * *